(12) United States Patent
Shinomiya

(10) Patent No.: US 8,092,273 B2
(45) Date of Patent: Jan. 10, 2012

(54) UNDERWEAR FOR LOWER PARTS

(75) Inventor: Yumi Shinomiya, Kobe (JP)

(73) Assignee: Indy & Associate, Kobe-shi (JP)

( * ) Notice: Subject to any disclaimer, the term of this patent is extended or adjusted under 35 U.S.C. 154(b) by 690 days.

(21) Appl. No.: 11/817,218

(22) PCT Filed: Feb. 24, 2006

(86) PCT No.: PCT/JP2006/303422
§ 371 (c)(1),
(2), (4) Date: Nov. 18, 2008

(87) PCT Pub. No.: WO2006/093044
PCT Pub. Date: Sep. 8, 2006

(65) Prior Publication Data
US 2009/0077720 A1    Mar. 26, 2009

(30) Foreign Application Priority Data
Feb. 28, 2005  (JP) ................. 2005-052586

(51) Int. Cl.
*A41C 3/00* (2006.01)
(52) U.S. Cl. ................. 450/97; 450/98; 450/100; 2/408
(58) Field of Classification Search ........... 450/97, 450/98, 100, 101, 122–124, 131, 114–118; 2/228, 227, 400–403, 406
See application file for complete search history.

(56) References Cited

U.S. PATENT DOCUMENTS

| | | |
|---|---|---|
| 2,763,009 A | 9/1956 | Blatt |
| 4,475,552 A | 10/1984 | Yoshihara |
| 4,476,895 A | 10/1984 | Shibusawa |
| 4,698,847 A * | 10/1987 | Yoshihara ........................ 2/69 |
| 5,699,559 A * | 12/1997 | Sano ................................ 2/67 |
| 5,876,395 A * | 3/1999 | Hart et al. ...................... 604/393 |
| 6,159,070 A * | 12/2000 | Schwartz et al. ............. 450/155 |
| 6,243,880 B1 | 6/2001 | Lyden |
| 6,592,428 B2 * | 7/2003 | Smith ........................... 450/134 |
| 6,728,973 B1 * | 5/2004 | Webley et al. .................... 2/400 |

(Continued)

FOREIGN PATENT DOCUMENTS
JP    63-14833    4/1988

(Continued)

OTHER PUBLICATIONS

International Search Report for Application No. PCT/JP2006/303422, dated Apr. 18, 2006.

(Continued)

*Primary Examiner* — Gloria Hale
(74) *Attorney, Agent, or Firm* — Marshall, Gerstein & Borun LLP (57) ABSTRACT

Lower underwear to be put on a body for intimate contact therewith for the purpose of correcting distortion of the pelvis. The lower underwear is provided with a tightening band passing a right pubis proximity portion, a right anterior superior iliac spine proximity portion, a sacrum proximity portion, a left anterior superior iliac spine proximity portion and a left pubis proximity portion in this order when the lower underwear is put on the body. The lower underwear provided with such a band is capable of gradually correcting distortion of the pelvis and the like by tightening the pelvis without applying pressure on the abdomen.

11 Claims, 9 Drawing Sheets

U.S. PATENT DOCUMENTS 7,631,366 B2 * 12/2009 Oyama et al. .................. 2/228
7,670,205 B2 *  3/2010 Oyama et al. ................. 450/97
7,757,307 B2 *  7/2010 Wong .............................. 2/228

FOREIGN PATENT DOCUMENTS

| JP | 2-182903 | 7/1990 |
| JP | 06-007394 | 1/1994 |
| JP | 3006642 | 11/1994 |
| JP | 07-003505 | 1/1995 |
| JP | 2001-192903 | 7/2001 |
| JP | 2001-262409 | 9/2001 |
| JP | 2001-276129 | 10/2001 |
| JP | 2002-263127 | 9/2002 |
| WO | WO-2006/006457 | 1/2006 |
| WO | WO-2006/033394 | 3/2006 |

OTHER PUBLICATIONS

Supplementary European Search Report for EP 06 71 4561, mailed Mar. 11, 2009.

* cited by examiner

UNDERWEAR FOR LOWER PARTS

TECHNICAL FIELD

The present invention relates to lower underwear having a power tape for redressing the pelvis from an open state.

BACKGROUND ART

As is often the case, distortions occur in a human body because of aging, living habits, long-time work with an unnatural posture, or the like, causing health disorder or the like to occur. Among such distortions, distortion of the pelvis causes a considerably large part of symptoms including health disorder, lumbago, backbone distortion, and obesity. In order to correct the distortion of the pelvis, it is a general practice to tighten a body part extending from the buttocks to the abdomen by the use of a member having a large elastic force (stretch force). A large number of inventions have been made concerning supporters and underwear for correcting the distortion of the pelvis. Examples of such inventions hitherto made include inventions of the type adapted to tighten the body part extending from the buttocks to the abdomen by means of a girdle (see Japanese Patent Laid-Open Publication No. 2002-263127, for example), inventions of the type adapted to tighten a body part adjacent the waist portion of underpants by means of a band (see Japanese Registered Utility Model Publication No. 3006642, for example), and inventions of the type adapted to tighten the abdomen and the great trochanters of the femurs (see Japanese Patent Laid-Open Publication No. HEI 6-7394, for example).

In tightening the whole or part of the pelvis, however, the abdomen, the buttocks and the great trochanters of the femurs are necessarily tightened at the same time, which often imparts the user with a sensation of pressure and a difficulty in body movements more strongly than necessary. A disclosed example of the present invention may provide lower underwear which is capable of relieving the sensation of pressure and the difficulty in body movements.

SUMMARY

In order to solve the above-described problem, a disclosed example of the present invention provides lower underwear to be put on a body for intimate contact therewith, the lower underwear comprising a power tape extending along the lower underwear from a sacrum proximity portion of the lower underwear to abdomen proximity portions situated on the front side of the lower underwear, the power tape further extending along the lower underwear from the abdomen proximity portions to right and left pubis proximity portions of the lower underwear. Such lower underwear is capable of gradually correcting distortion of the pelvis and the like by tightening the pelvis without applying pressure onto the abdomen.

In the lower underwear to be put on a body for intimate contact therewith, the power tape may pass the right pubis proximity portion, a right anterior superior iliac spine proximity portion, the sacrum proximity portion, a left anterior superior iliac spine proximity portion and the left pubis proximity portion of the lower underwear in this order. The lower underwear with such a feature is capable of gradually correcting distortion of the pelvis and the like more effectively by tightening the pelvis without applying pressure onto the abdomen.

In the lower underwear to be put on a body for intimate contact therewith, the power tape may pass a right ischium proximity portion, the right pubis proximity portion, a right anterior superior iliac spine proximity portion, the sacrum proximity portion, a left anterior superior iliac spine proximity portion, the left pubis proximity portion and a left ischium proximity portion of the lower underwear in this order. The lower underwear with such a feature has an increased tightening force and hence is capable of gradually correcting distortion of the pelvis and the like by tightening the pelvis more strongly without applying pressure onto the abdomen.

In the lower underwear to be put on a body for intimate contact therewith, the power tape may pass a left ischium proximity portion, the night pubis proximity portion, a right anterior superior iliac spine proximity portion, a sacrum proximity portion, a left anterior superior iliac spine proximity portion, the left pubis proximity portion and a right ischium proximity portion of the lower underwear in this order. The lower underwear with such a feature is capable of gradually correcting distortion of the pelvis and the like by tightening the pelvis with a minimum tightening force without applying pressure onto the abdomen. At the same time, the lower underwear is capable of redressing the pelvis into its normal condition by supporting a group of weakened muscles associated with the pelvis by a crotch portion of the lower underwear where the power tape crosses.

The lower underwear may further comprise: a second member forming an upper rear portion and right and left side portions of the lower underwear for stably fixing the waist of the body; and a substantially T-shaped first member extending continuously from the second member to form a front portion of the lower underwear, the first member comprising a material having such a small elastic force as not to impose pressure on the abdomen of the body, wherein the first and second members are provided with the power tape. The lower underwear with such a feature is capable of supporting the tightening force at the waist while relieving a sensation of tightness by failing to apply pressure onto the abdomen.

The first member may be formed to have a smaller elastic force than the second member. This feature makes it possible to further relieve the sensation of tightness imparted to the abdomen.

A disclosed example of the present invention also provides lower underwear to be put on a body for intimate contact therewith, the lower underwear comprising: a pair of power tapes, one of which extends from a left pubis proximity portion to a right ischium proximity portion of the lower underwear and the other of which extends from a right pubis proximity portion to a left ischium proximity portion of the lower underwear to cross the former power tape. Such lower underwear is capable of redressing the pelvis into its normal condition with a small tightening force.

A disclosed example of the present invention present invention also provides lower underwear to be put on a body for intimate contact therewith, the lower underwear comprising: a pair of power tapes provided in a crotch portion of the lower underwear, wherein when the lower underwear is placed on a flat surface with its front side up, the power tapes cross each other on the front side of the underwear.

It is possible that one of the power tapes extends from a left pubis proximity portion to a right ischium proximity portion of the lower underwear and the other of the power tapes extends from a right pubis proximity portion to a left ischium proximity portion of the lower underwear to cross the former power tape.

A disclosed example of the present invention present invention also provides lower underwear to be put on a body for intimate contact therewith, the lower underwear comprising: a pair of power tapes provided in a crotch portion of the lower underwear, wherein when the lower underwear is placed on a flat surface with its front side up, the power tapes extend on right and left sides of the crotch portion separately with a predetermined spacing therebetween on the front side of the underwear.

It is possible that the power tapes extend separately with the predetermined spacing therebetween in such a manner that one of the power tapes extends from a left pubis proximity portion to a left ischium proximity portion of the lower underwear and the other of the power tapes extends from a right pubis proximity portion to a right ischium proximity portion of the lower underwear.

In the lower underwear, it is possible that: the crotch portion is joined with an abdomen portion by a front juncture and with a buttock portion by a rear juncture; and the power tapes extend between the front juncture and the rear juncture.

The user can correct distortion of the pelvis without feeling too strong a sensation of pressure by merely putting on the lower underwear of the present invention as in the case of common lower underwear. For this reason, gradual improvements can be made in health disorder, lumbago, obesity and the like. Further, the lower underwear is capable of preventing the pelvis from being distorted.

BEST MODE FOR CARRYING OUT THE INVENTION

One embodiment of the present invention will be described with reference to the drawings.

Figure 1A:
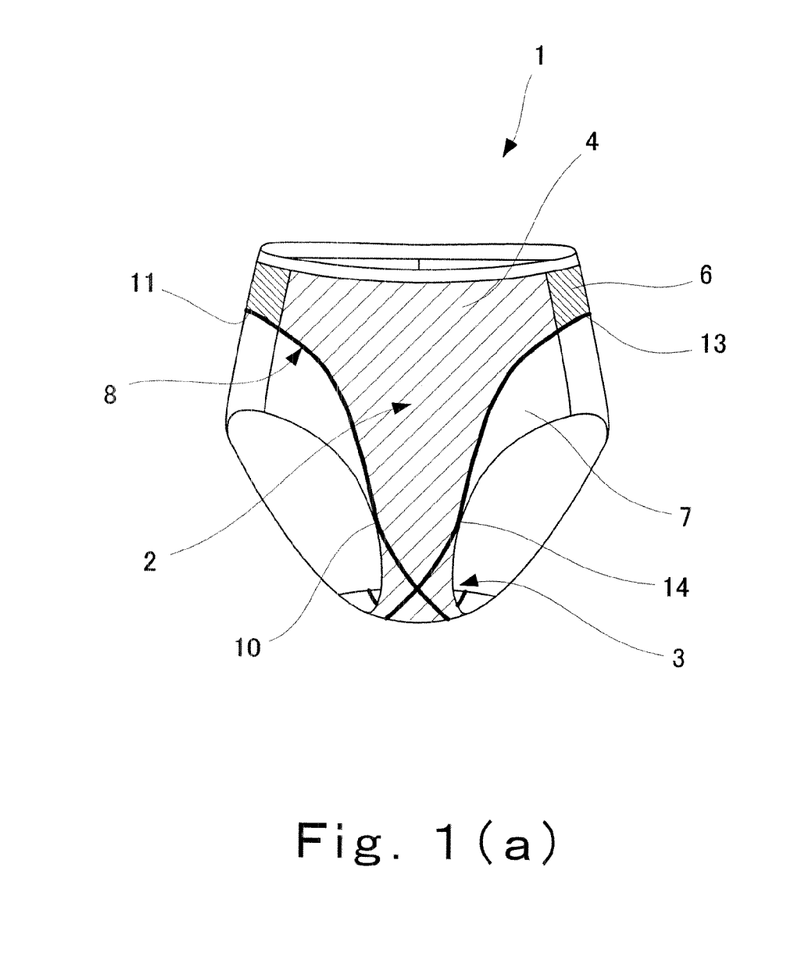
FIG. 1(a) is a front elevational view and FIG. 1(b) is a rear elevational view.
Figure 1B:
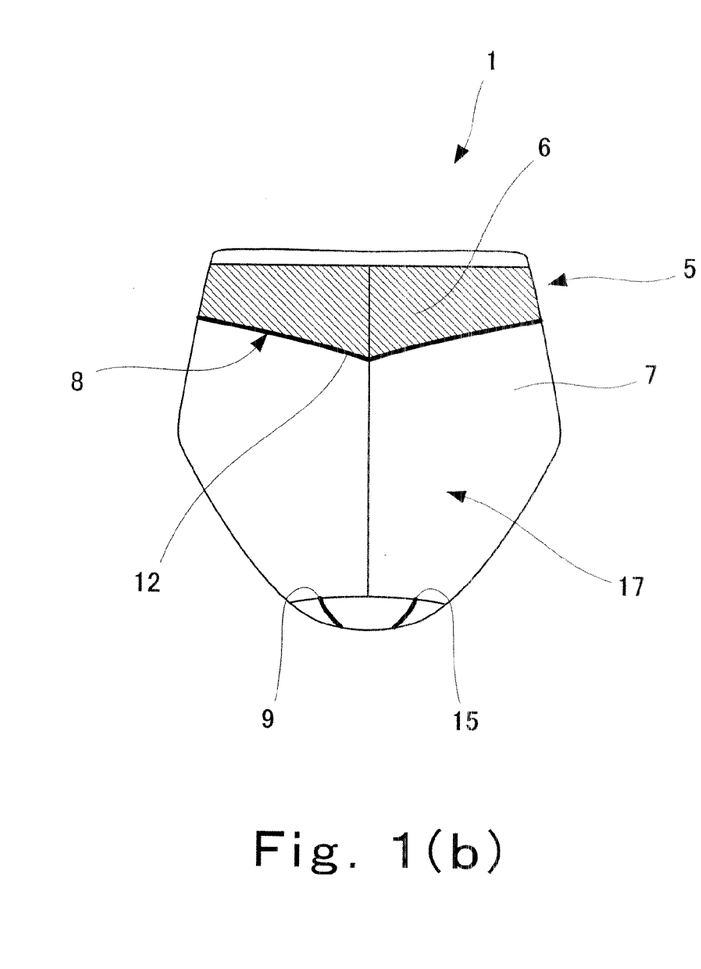

FIG. 1 illustrates the structure of lower underwear according to the present invention; specifically, FIG. 1(a) is a front elevational view and FIG. 1(b) is a rear elevational view.

As shown in FIGS. 1(a) and 1(b), the lower underwear 1 comprises members which are different from each other in properties (characteristics of material). A first member 4 is used to form a substantially inverted triangular portion in the proximity of an abdomen portion 2 and a portion in the proximity of a crotch (crotch gusset) portion 3. A second member 6 extends continuously from the first member 4 to side portions 5. A third member 7 is used to form the remaining portions other than the first and second members 4 and 6. Since the first member 4 is mainly used to form the abdomen portion 2, the first member 4 comprises a material that is stretchable but has a small elastic force so as not to impart a sensation of pressure onto the abdomen portion 2. On the other hand, the second member 6 comprises a material that is stretchable and has a large elastic force because the second member 6 needs to support a force exerted on the first member 4 by a portion extending from a sacrum proximity portion 12 to right and left anterior superior iliac spine proximity portions 11 and 13. As to elastic force, the relation: second member 6>first member 4☐third member 7 holds. The second member 6, which supports the entire pelvis by the portion extending from the sacrum proximity portion 12 to the right and left anterior superior iliac spine proximity portions 11 and 13, is the largest in elastic force. The third member 7, which forms a highly movable portion, is the smallest in elastic force. A power tape 8 comprising a stretchable material for exerting a tightening force is provided as extending along the lower edges of the first and second members 4 and 6 (along the boundary lines between the first member 4 and the third member 7 and between the second member 6 and the third member 7) so as to exert such a force as to embrace the pelvis 39 inwardly forwardly.

Figures 2A, 2B:
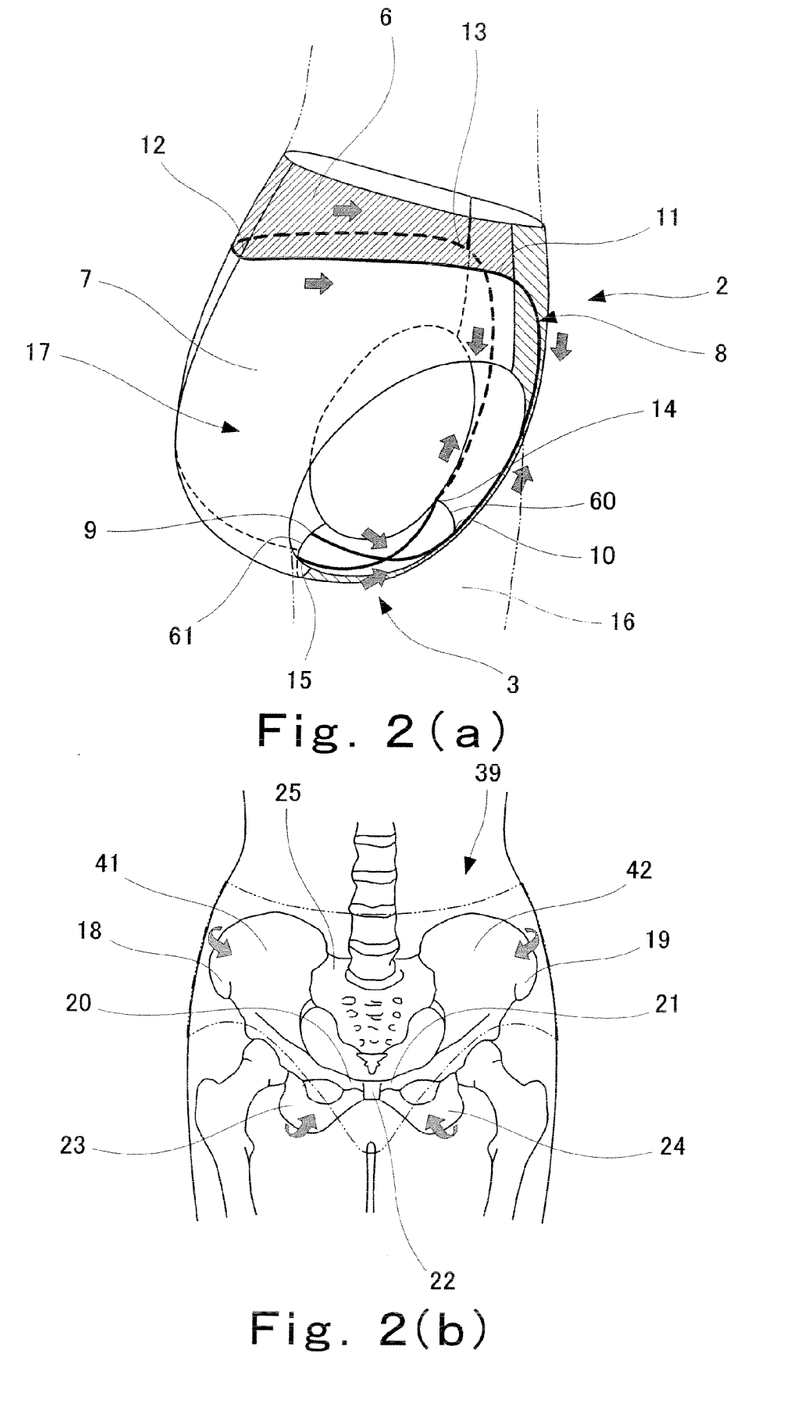
FIG. 2(a) is a right perspective view and FIG. 2(b) is a front elevational view.

FIG. 2 illustrates the lower underwear in a put-on condition; specifically, FIG. 2(a) is a right perspective view and FIG. 2(b) is a front elevational view.

As shown in FIG. 2, the lower underwear 1 has the power tape 8 extending to pass a left ischium proximity portion 9, a right pubis proximity portion 10, a right anterior superior iliac spine proximity portion 11, a sacrum proximity portion 12, a left anterior superior iliac spine proximity portion 13, a left pubis proximity portion 14 and a right ischium proximity portion 15 in this order. The power tape 8 forms a tightening line (hereinafter will be referred to as "pelvis line") which extends along such a passage as not to interfere with changes of body (including expansion of the abdomen 2 due to taking a meal and a like change) and with movements of the legs 16 during exercise thereby minimizing the tightening force of the lower underwear 1 to be exerted on the body. Since the power tape 8 extends to cross itself at the crotch portion 3, a force is exerted to tighten the lower side of the pelvis 39 inwardly forwardly of the body when the lower underwear 1 is in a put-on condition. Similarly, the upper side of the pelvis 39 is tightened inwardly forwardly of the body by the power tape 8 on the pelvis line. The tightening force works in directions indicated by arrows (i.e., directions in which the power tape 8 contracts). Specifically, the tightening force works forwardly at the sacrum proximity portion 12, downwardly at the right and left anterior superior iliac spine proximity portions 11 and 13, upwardly at the right and left pubis proximity portions 10 and 14, and forwardly at the right and left ischium proximity portions 15 and 9 in directions crossing each other.

Such a tightening force causes the third member 7 in the proximity of the buttocks 17 to embrace the pelvis 39 by substantially uniform forward force exerted on the pelvis 39. Accordingly, as shown in FIG. 2(b), the right and left anterior superior iliac spines 18 and 19 located on the upper side of the pelvis 39 receive forces working in arrow directions toward the pubic symphysis 22 between the right and left pubes 20 and 21, while at the same time the right and left ischia 23 and 24 receive forces working in arrow directions toward the pubic symphysis 22. Thus, if the pelvis 39 is in a displaced condition (with displacement between the sacrum 25 and the right and left ilia 41 and 42 and displacement between the right and left pubes 20 and 21), the lower underwear 1 acts to correct such displacement of the pelvis 39. If the pelvis 39 is not in a displaced condition, the lower underwear 1 acts to prevent the occurrence of such displacement. This action makes it possible to gradually correct distortion of the pelvis 39 due to long-time work with an unnatural posture or a like cause, thereby to relieve lumbago, health disorder or the like.

It is possible that the power tape 8 extends to form parallel tightening lines on the crotch portion 3 by passing the right ischium proximity portion 15, the right pubis proximity portion 10, the right anterior superior iliac spine proximity portion 1, the sacrum proximity portion 12, the left anterior superior iliac spine proximity portion 13, the left pubis proximity portion 14 and the left ischium proximity portion 9 in this order (not shown), the tightening force received by the crotch 3 of the body from the power tape 8 can be relieved.

Since vertical forces are exerted on the front side of the lower underwear 1 of the above-described structure, the lower underwear 1 is displaced due to exercise or the like as the case may be. In order to prevent such displacement, the force of the power tape 8 is supported by the second member 6 which is provided between the sacrum proximity portion 12 and the left anterior superior iliac spine proximity portion 13 and between the sacrum proximity portion 12 and the right anterior superior iliac spine proximity portion 11 to cover a corresponding body part that changes (expands and contracts) a little. Thus, the lower underwear 1 in a stabilized position is capable of exerting uniform force on the pelvis 39.

Figure 3:
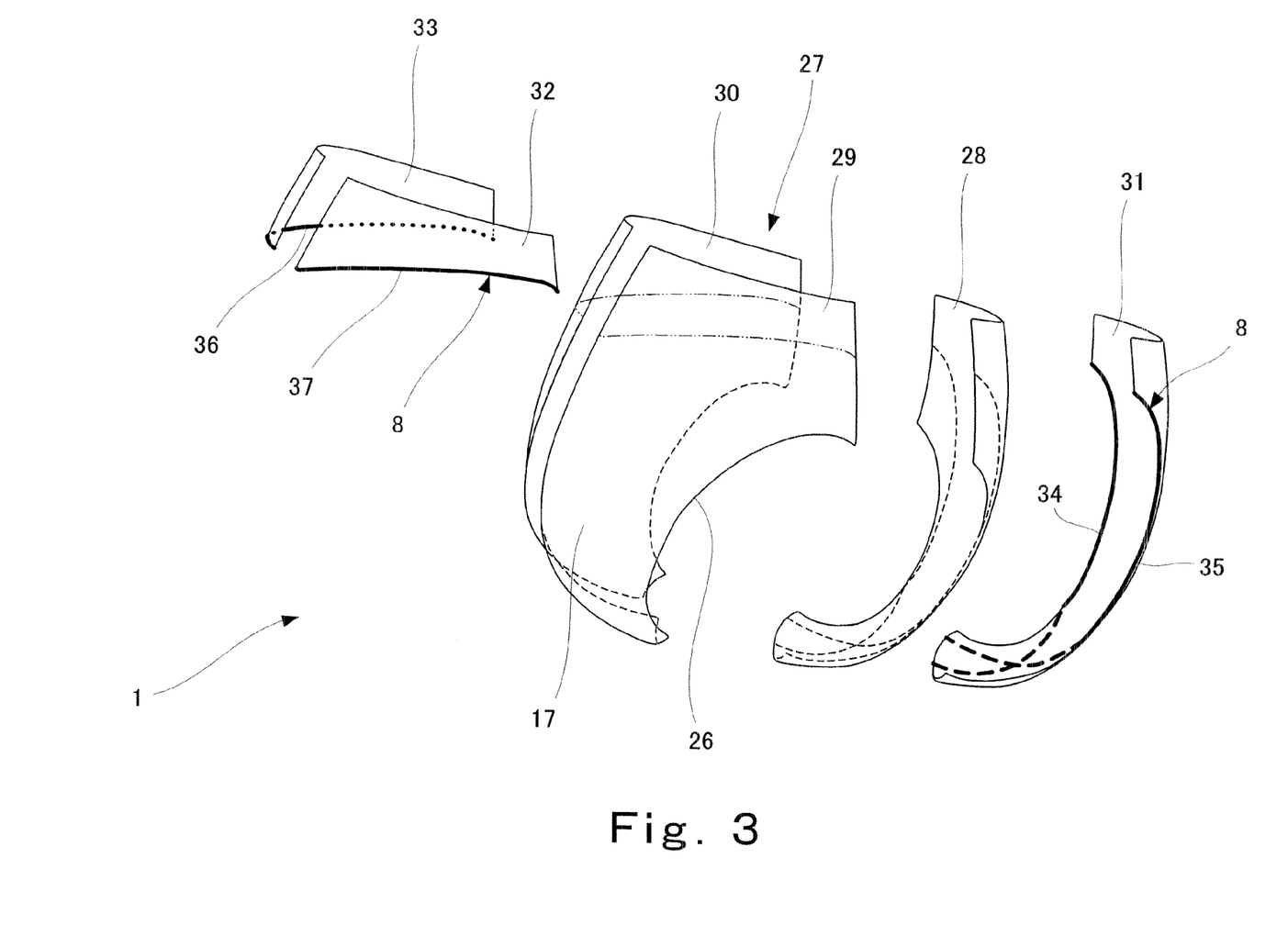
FIG. 3 is an exploded perspective view showing members forming lower underwear according to another embodiment of the present invention.

FIG. 3 is an exploded perspective view showing members forming lower underwear according to another embodiment of the present invention.

The tightening force of the lower underwear 1 can be varied by the use of members which are different in properties from each other and are sewn either together or in a superposed fashion, as shown in FIG. 3. Active regions of the lower underwear 1 including the buttock portion 17 and leg opening portions 26 are formed of a base member 27 comprising a highly flexible material (third member) only so as not to interfere with movements of the legs during walking or exercise. This base member 27 includes a front-side member 28, a right-side member 29 and a left-side member 30, which are formed of the third member, hence, have the same properties. A front reinforcement member 31, a right reinforcement member 32 and a left reinforcement member 33 are superposed on the base member 27 by suture. The front reinforcement member 31 is located to cover a substantially central portion of the front-side member 28 on the front side; the right reinforcement member 32 located to cover the whole of an upper edge portion of the right-side member 29; and the left reinforcement member 33 located to cover the whole of an upper edge portion of the left-side member 30. The front reinforcement member 31, left reinforcement member 33 and right reinforcement member 32 have respective power tapes 8. The power tape 8 of the front reinforcement member 31 extends along right and left edges 34 and 35, while those of the right and left reinforcement members 32 and 33 extend along lower edges 37 and 36 of the respective reinforcement members 32 and 33. Such an arrangement is capable of adjusting the tightening force to the wearer by merely changing the properties of each of the front reinforcement member 31, left reinforcement member 33 and right reinforcement member 32.

Figure 4A:
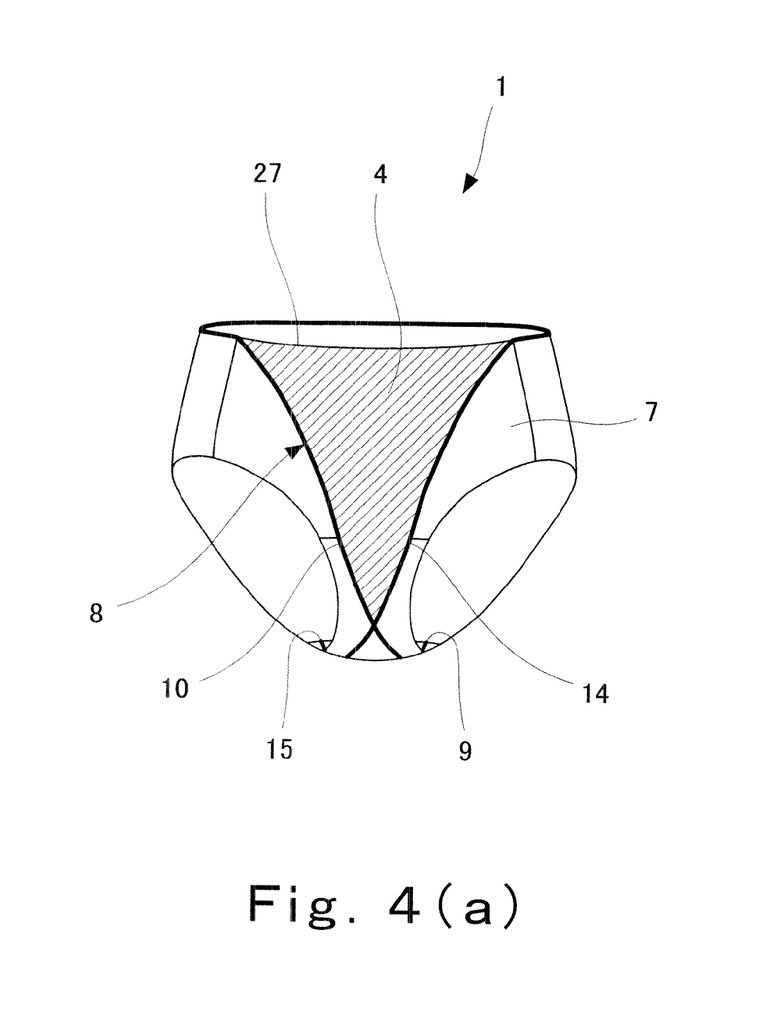
FIG. 4(a) is a front elevational view and FIG. 4(b) is a rear elevational view.
Figure 4B:
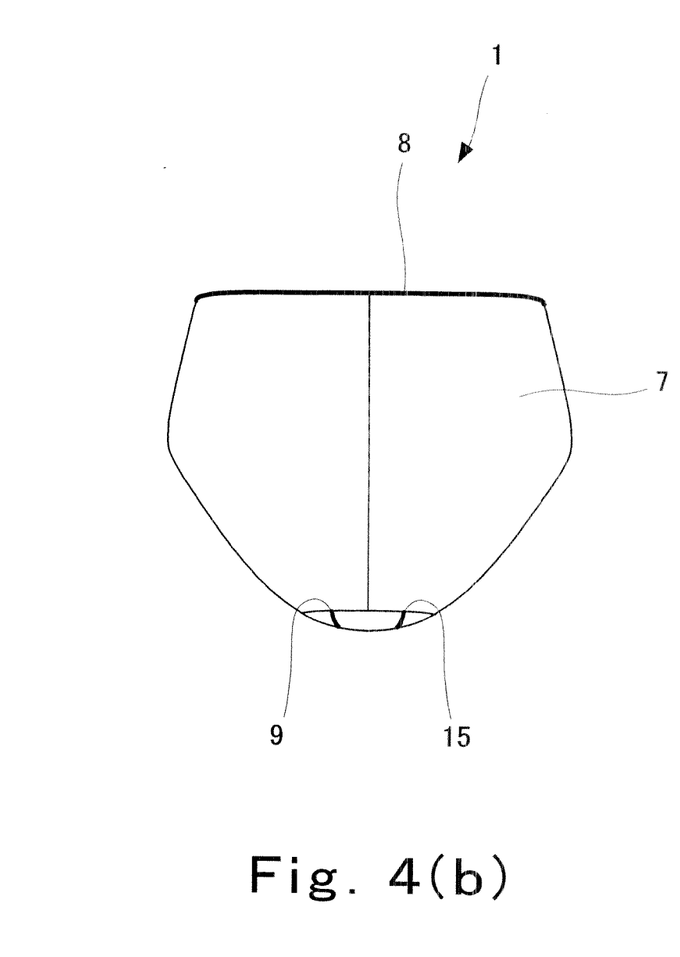

FIG. 4 illustrates lower underwear according to another embodiment of the present invention; specifically, FIG. 4(a) is a front elevational view and FIG. 4(b) is a rear elevational view.

As shown in FIG. 4(a), the lower underwear 1, which has its upper edge formed to be positioned on the right and left anterior superior iliac spine proximity portions 11 and 13, has a waist proximity portion of the power tape 8 which is positioned to coincide with the upper edge of the lower underwear 1 and is free of the second member 6 (see FIG. 1) extending from the right and left anterior superior iliac spine proximity portions 11 and 13 to the sacrum proximity portion 12. As compared with the lower underwear 1 having the second member 6 positioned in the sacrum proximity portion 12 as shown in FIG. 2, the arrangement of interest cannot support the tightening force of the power tape 8 by the waist portion (including the sacrum proximity portion 12 and the right and left anterior superior iliac spine proximity portions 11 and 13) and, hence, the power tape 8 exerts a decreased tightening force. However, the power tape 8 passing on the pelvis line exerts the force of tightening the upper and lower sides of the pelvis 39 inwardly forwardly of the body, hence, functions like the lower underwear 1 shown in FIG. 2.

Figure 5A:
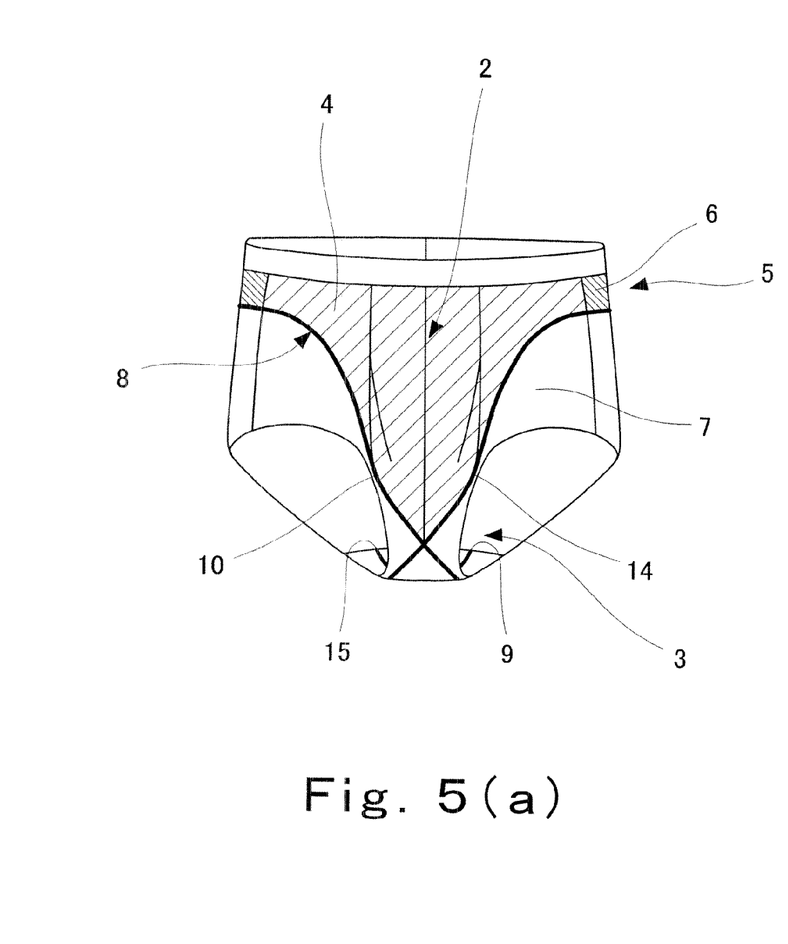
Figure 5B:
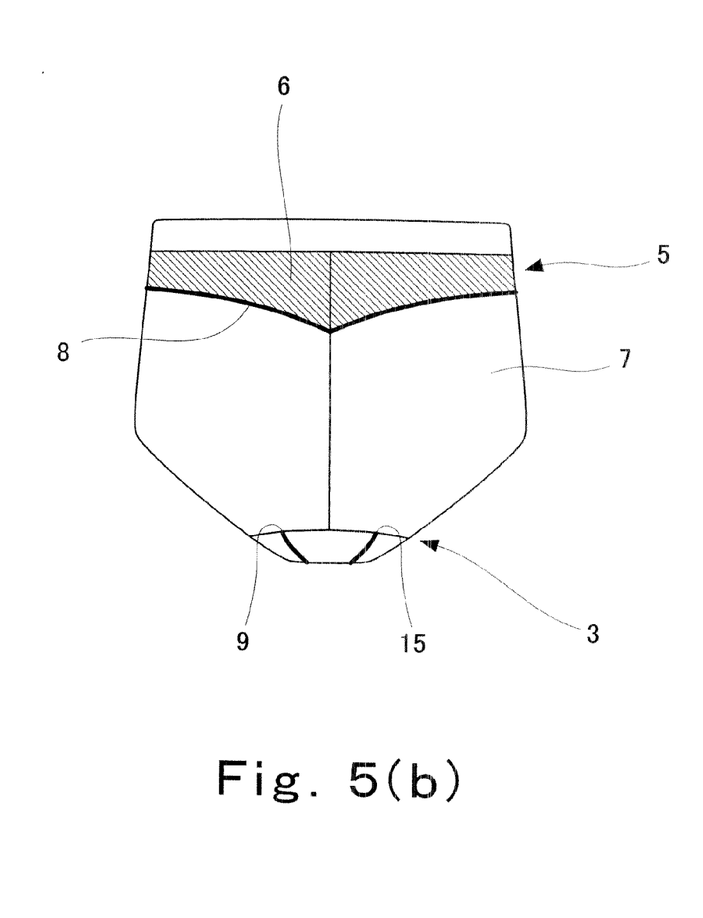

FIG. 5 illustrates lower underwear for men according to another embodiment of the present invention; specifically, FIG. 5(a) is a front elevational view and FIG. 5(b) is a rear elevational view.

As shown in FIG. 5(a), the lower underwear 1 comprises the first member 4, the second member 6 and the third member 7, the first member 4 being used to form a substantially T-shaped portion in the proximity of the abdomen portion 2 and a portion in the proximity of the crotch portion 3. The second member extends continuously from the first member to the side portions 5 as shown in FIG. 1(b). The third member is used to form the remaining portion of the lower underwear 1 other than the first and second members. The substantially T-shaped portion of the first member is three-dimensionally shaped so as to accommodate the pubic region of a man therein. The lower underwear 1 provided with power tape 8 on the first and second members is capable of exerting the force of tightening the lower side of the pelvis 39 inwardly forwardly of the body as well as the force of tightening the upper side of the pelvis 39 inwardly forwardly of the body.

Figure 6A:
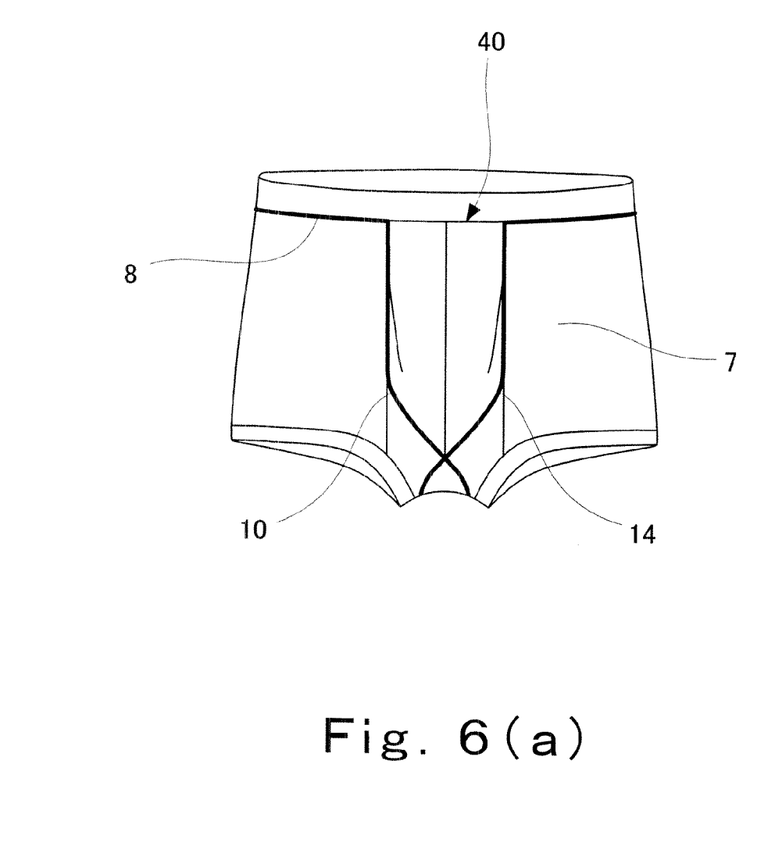
FIG. 6(a) is a front elevational view and FIG. 6(b) is a rear elevational view.
Figure 6B:
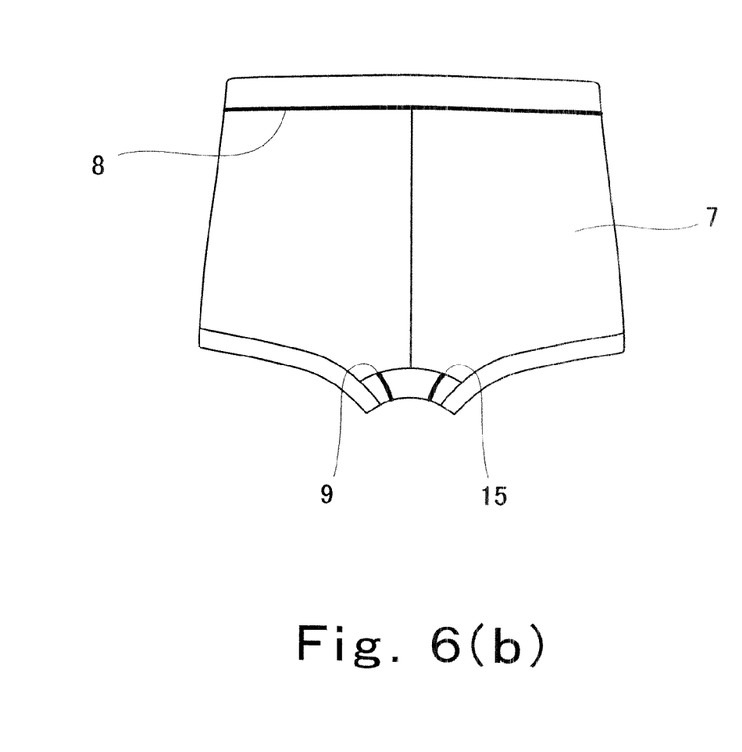

FIG. 6 illustrates lower underwear free of the second member; specifically, FIG. 6(a) is a front elevational view and FIG. 6(b) is a rear elevational view.

As shown in FIG. 6(a), the lower underwear 1 is free of the second member shown in FIG. 5 and is provided with the power tape 8. Since the power tape 8 extends to pass on the pelvis line, the lower underwear 1 exerts the force of tightening the upper and lower sides of the pelvis 39 inwardly forwardly of the body. Here, the pelvis line extends from the right and left anterior superior iliac spine proximity portions 11 and 13 toward the center of the body and, hence, the lower underwear 1 exerts an increased tightening force in the proximity of the abdomen as compared with the underwear shown in FIG. 5. However, since the power tape 8 has a discontinuous portion 40 where the power tape 8 is discontinuous in the abdomen portion (between the right and left anterior superior iliac spine proximity portions 11 and 13), the discontinuous portion 40 accommodates changes of the abdomen (expansion and contraction and like changes) and hence makes it possible to relieve a sensation of tightness imparted to the abdomen.

Figure 7A:
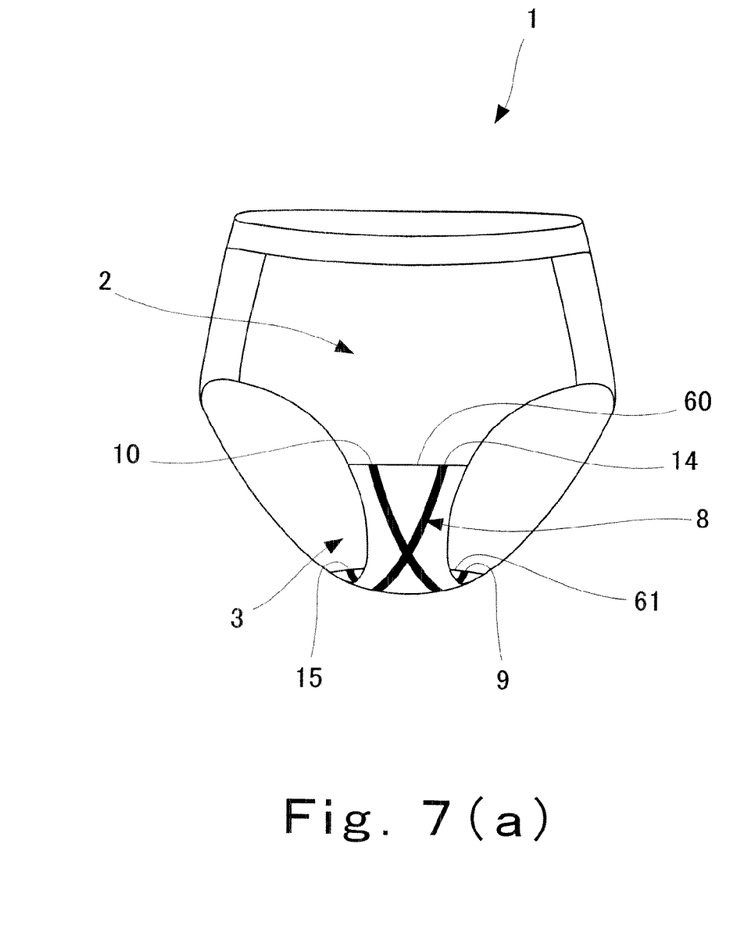
FIG. 7(a) is a front elevational view and FIG. 7(b) is a rear elevational view.
Figure 7B:
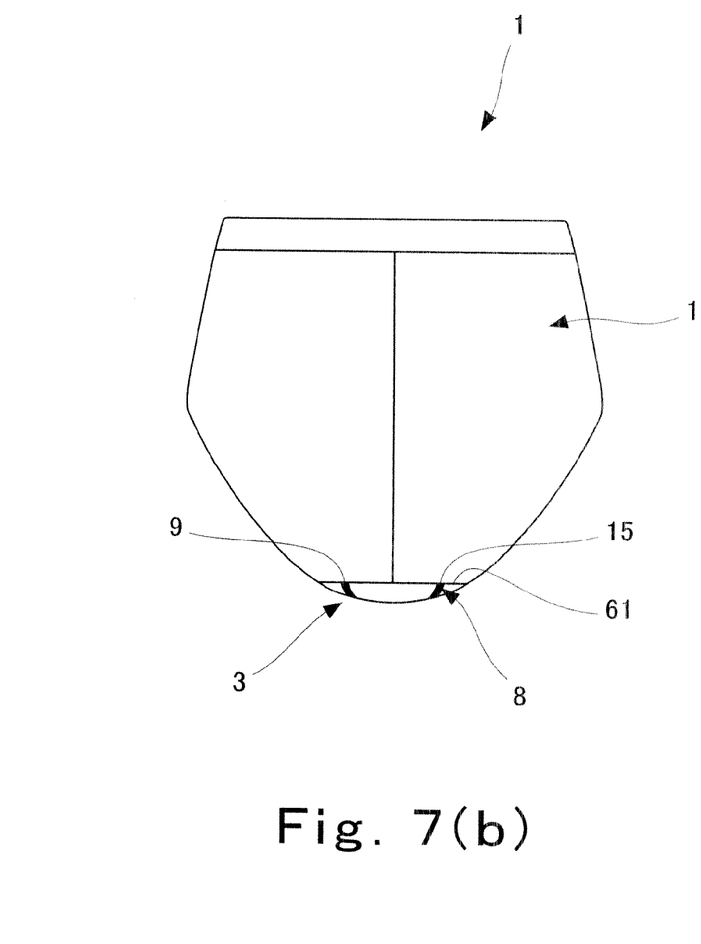

FIG. 7 illustrates lower underwear having power tapes as shown in FIG. 1 which extend only in the crotch portion to cross each other according to another embodiment of the present invention; specifically, FIG. 7(a) is a front elevational view and FIG. 7(b) is a rear elevational view. FIG. 8 illustrates lower underwear having power tapes which extend only in the crotch portion shown in FIG. 1 on the right and left sides of the crotch portion separately with a predetermined spacing therebetween according to another embodiment of the present invention; specifically, FIG. 8(a) is a front elevational view and FIG. 8(b) is a rear elevational view.

As shown in FIGS. 7(a) and 7(b) showing the lower underwear 1 placed on a flat surface with its front side up, the power tapes 8 cross each other on the front side of the lower underwear 1. The lower underwear 1 has a front juncture 60 joining the abdomen portion 2 and the crotch portion 3 together and a rear juncture 61 joining the crotch portion and the buttock portion. One of the power tapes 8 extends from the left pubis proximity portion 14 to the right ischium proximity portion 15 of the lower underwear 1, while the other power tape 8 extends from the right pubis proximity portion 10 to the left ischium proximity portion 9 of the lower underwear 1 to cross the counterpart power tape 8. The lower underwear 1 provided with the power tapes 8 only in the crotch portion 3 is smaller in such a tightening force as to embrace the pelvis 39 than the lower underwear having the power tape 8 extending up to the waist portions as shown in FIG. 1. When compared with lower underwear that is already on market, however, the lower underwear 1 provided with the power tapes 8 in the crotch portion 3 exerts an increased tightening force to embrace the pelvis 39 (see FIG. 2) by the power tapes 8 drawing the front-side member and the rear-side member toward each other, thereby making it possible to redress the pelvis into its normal position. At the same time, the lower underwear 1 is capable of preventing or improving ptosis of the internal organs or muscles, hence, redressing the body into the normal condition by the power tapes 8 supporting the internal organs or muscles sagging with aging at the pelvis 39. Further, since the power tapes cross each other in the crotch portion as in FIG. 1 so that the cross point coincides with a meridian point of the body, the lower underwear 1 is capable of not only redressing the pelvis into its distortion-free normal condition but also causing the body (physical condition) to restore its normal condition by stimulating meridian points coinciding with or adjacent to the cross portion.

Figure 8A:
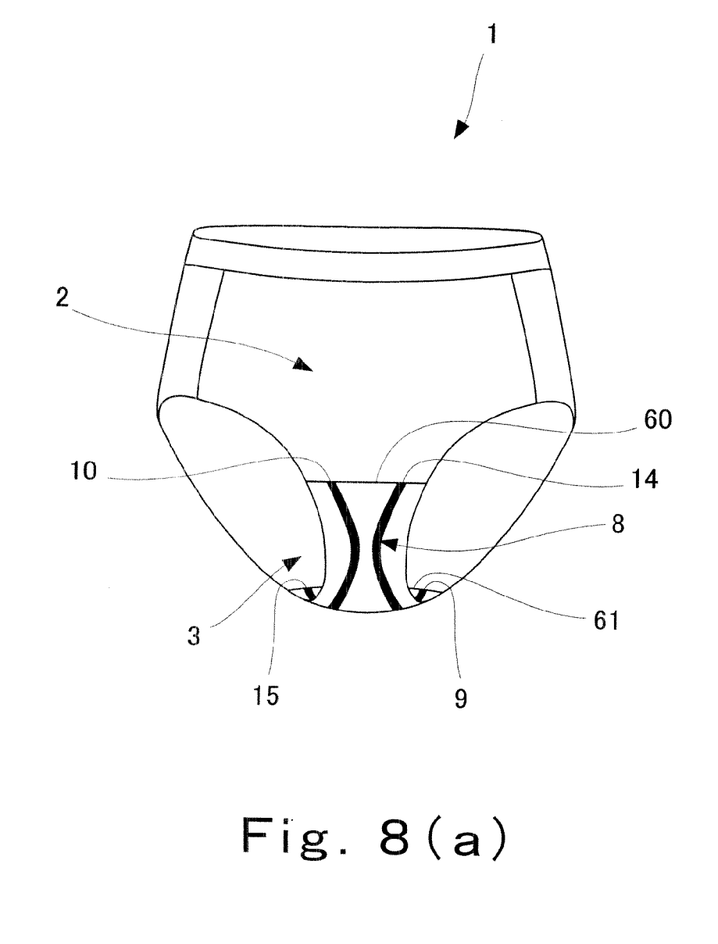
FIG. 8(a) is a front elevational view and FIG. 8(b) is a rear elevational view.
Figure 8B:
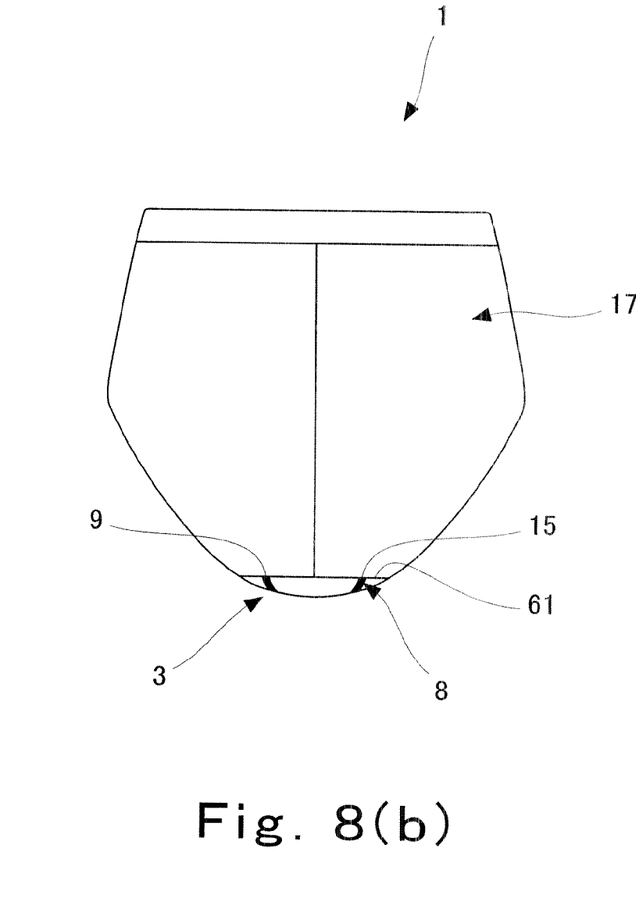

By being provided with the power tapes 8 only in the crotch portion separately with a predetermined spacing from each other on the right and left sides of the crotch portion as shown in FIGS. 8(a) and 8(b), more preferably, with their respective middle portions brought close to each other as shown in FIG. 8(a), the lower underwear 1 exerts a larger tightening force than common lower underwear, though the pelvis tightening force of such lower underwear 1 is smaller than that of the lower underwear 1 having the power tapes 8 crossing each other like X as shown in FIG. 7. Further, since the power tapes 8 extend adjacent meridian points, the lower underwear 1 is capable of not only redressing the pelvis into its distortion-free normal condition but also causing the body (physical condition) to restore its normal condition by stimulating points adjacent to the meridian points.

Figure 9A:
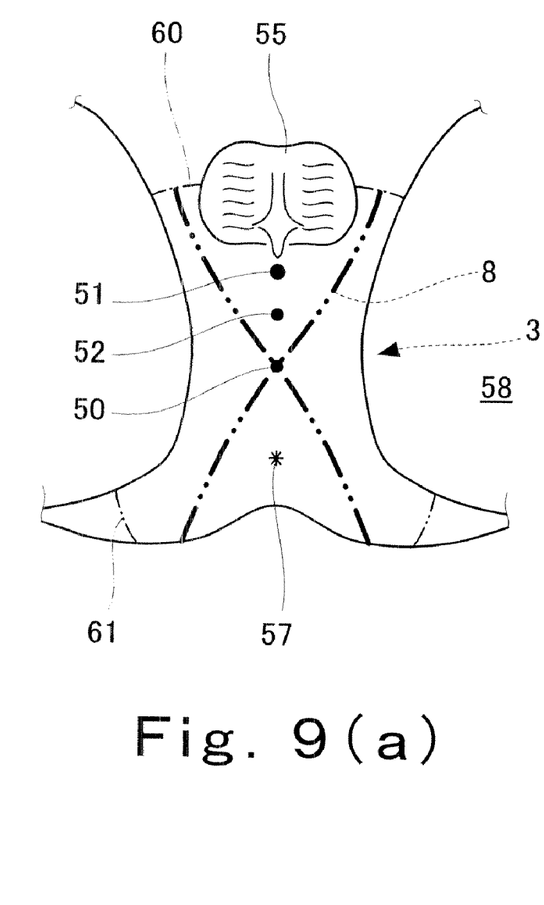
FIG. 9(a) illustrates the positional relation in the case of a man and FIG. 9(b) illustrates the positional relation in the case of a woman.
Figure 9B:
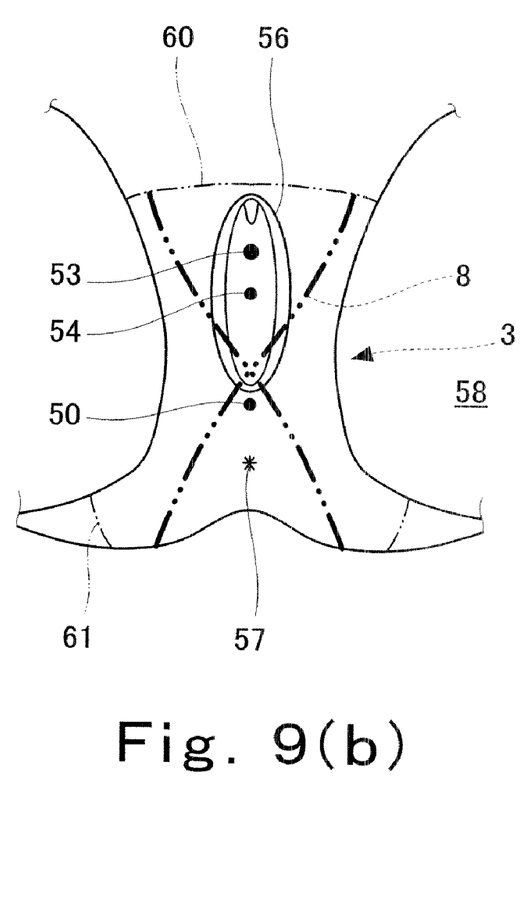

FIG. 9 illustrates the positional relation between the crotch of a human and power tapes; specifically, FIG. 9(a) illustrates the positional relation in the case of a man and FIG. 9(b) illustrates the positional relation in the case of a woman.

As shown in FIGS. 9(a) and 9(b), meridian points which are located adjacent the cross point of the power tapes 8 and between the scrotum 55 or large pudendal lips 56 and the anus 57 include Ein 50, Innokaomon 51, Notei 52, Yoro 53, Gyokumonto 54, and like meridian points. The power tapes 8 stimulate these meridian points or points adjacent to the respective meridian points to smooth the blood circulation or the lymph circulation, thereby improving poor circulation in the lower part of the body, swelling of the legs and feet, lumbago and like symptoms. Depending on persons, improvement can be made in distortion of the body, obesity, or like symptoms. The power tapes 8 shown in FIG. 9(a) or 9(b) cross each other or are brought close to each other at a location between Innokaomon 51 or Yoro 53 and the anus 57, preferably, at a location adjacent to Ein 50 as shown and extend upwardly and downwardly from that location in the figures in directions away from each other so as to be shaped X or separated from each other with a predetermined spacing therebetween. Since the right and left thighs 58 are brought closer to each other to press the crotch portion 3 of the lower underwear inwardly when the lower underwear is put on the body, the power tapes 8 are brought closer to Ein 50, Innokaomon 51, Notei 52, Yoro 53, Gyokumonto 54, hence, allowed to stimulate these meridian points more easily.

When put on the body, the lower underwear thus structured has a pelvis line that connects the right pubis proximity portion and the left ischium proximity portion and a pelvis line that connects the left pubis proximity portion and the right ischium proximity portion. These pelvis lines cross each other at a point lying between the anus and the external urethral meatus in the case of a woman or between the anus and the under scrotum part in the case of a man, to support a group of weakened muscles associated with the pelvis at their cross point on the crotch portion. Thus, the lower underwear is capable of redressing the pelvis into its normal condition by a smaller tightening force, which leads to improvements in health disorder and the like. A similar effect can be obtained by changing knitting (knitted fabric or knitting yarn) instead of replacement of each member. A tape-shaped accessory material having a large elastic force, such as stretch rubber or stretchable tape, is used for the power tapes 8. However, if such an accessory material is unavailable, a kind of stitching using a stretchable yarn in sewing, such as 3-needle ornamental stitching, can be used for the power tapes 8 instead of the tape-shaped accessory material.

The lower underwear described above is not limited to underwear (underpants, shorts and the like) to be put on the body under outer clothing such as trousers, skirt or the like, but is applicable to training wear, swimsuits and like wear to be put on the body for intimate contact therewith (including integral wear covering both the upper and lower parts of the body).

INDUSTRIAL APPLICABILITY

The lower underwear of the present invention is applicable to clothing for intimate contact with the body, such as underpants, girdle, training wear, swimsuit, and like wear.

BRIEF DESCRIPTION OF DRAWINGS

FIG. 1 illustrates the structure of lower underwear according to the present invention; specifically.

FIG. 2 illustrates the lower underwear in a put-on condition; specifically.

FIG. 4 illustrates lower underwear according to another embodiment of the present invention; specifically.

FIG. 5 illustrates lower underwear for men according to another embodiment of the present invention; specifically, FIG. 5(a) is a front elevational view and FIG. 4(b) is a rear elevational view.

FIG. 6 illustrates lower underwear free of the second member shown in FIG. 5; specifically.

FIG. 7 illustrates lower underwear having power tapes as shown in FIG. 1 which are provided only in a crotch portion according to another embodiment of the present invention; specifically.

FIG. 8 illustrates lower underwear having power tapes which extend only in the crotch portion shown in FIG. 1 on the right and left sides of the crotch portion separately with a predetermined spacing therebetween according to another embodiment of the present invention; specifically.

FIG. 9 illustrates the positional relation between the crotch of a human and power tapes; specifically.

DESCRIPTION OF REFERENCE CHARACTERS

1 . . . lower underwear
2 . . . abdomen portion
3 . . . crotch portion
4 . . . first member
5 . . . side portion
6 . . . second member 7 ... third member
8 ... power tape
9 ... left ischium proximity portion
10 ... right pubis proximity portion
11 ... right anterior superior iliac spine proximity portion
12 ... sacrum proximity portion
13 ... left anterior superior iliac spine proximity portion
14 ... left pubis proximity portion
15 ... right ischium proximity portion
16 ... leg
17 ... buttock portion
18 ... right anterior superior iliac spine
19 ... left anterior superior iliac spine
20 ... right pubis
21 ... left pubis
22 ... pubic symphysis
23 ... right ischium
24 ... left ischium
25 ... sacrum
39 ... pelvis
40 ... discontinuous portion
41 ... right ilium
42 ... left ilium
50 ... Ein
55 ... scrotum
56 ... large pudendal lips
57 ... anus
60 ... front juncture
61 ... rear juncture

The invention claimed is:

1. Lower underwear to be put on a body for intimate contact therewith, comprising:
an abdomen portion of the lower underwear arranged to partially cover an abdomen of the body;
a crotch portion of the lower underwear including a width and arranged to partially cover a crotch of the body;
a buttock portion of the lower underwear including an area arranged to cover a buttock of the body;
a pair of power tapes provided at least in the crotch portion of the lower underwear, wherein when the lower underwear is arranged such that when placed on a flat surface with a front side up, said power tapes cross each other at an inner area of the crotch portion on the front side of the underwear without extending along an edge of the crotch portion; and
wherein the power tapes are arranged to apply a force to the crotch of the body such that the abdomen portion, the buttock portion, and the crotch portion having the power tapes are arranged to embrace the pelvis of the body.

2. The lower underwear according to claim 1, wherein one of said power tapes extends from a left pubis proximity portion to a right ischium proximity portion of the lower underwear, while the other of said power tapes extends from a right pubis proximity portion to a left ischium proximity portion of the lower underwear to cross the former power tape.

3. The lower underwear according to claim 1, wherein:
said crotch portion is joined with an abdomen portion by a front juncture and with a buttock portion by a rear juncture; and
said power tapes extend between said front juncture and said rear juncture.

4. The lower underwear according to claim 1, wherein the pair of power tapes extend along the lower underwear from a sacrum proximity portion of the lower underwear to the abdomen portion situated on the front side of the lower underwear, the pair of power tapes further extend along the lower underwear from the abdomen portion to a right pubis proximity portion and a left pubis proximity portion.

5. The lower underwear according to claim 4, wherein the pair of power tapes pass through, in order, the right pubis proximity portion, a right anterior superior iliac spine proximity portion, a sacrum proximity portion, a left anterior superior iliac spine proximity portion, and the left pubis proximity portion.

6. The lower underwear according to claim 1, wherein the pair of power tapes pass through, in order, a left ischium proximity portion, the right pubis proximity portion, a right anterior superior iliac spine proximity portion, the sacrum proximity portion, a left anterior superior iliac spine proximity portion, the left pubis proximity portion and a right ischium proximity portion.

7. The lower underwear according to claim 1, and further comprising:
a second member forming an upper rear portion, an upper right side portion, and an upper and left side portion, and arranged to stably fix a waist of the body; and
a substantially T-shaped first member extending continuously from the second member to form a front portion of the lower underwear, the first member comprising a material having such an elastic force as not to impose pressure on the abdomen of the body, wherein the first and second members are provided with the power tapes.

8. The lower underwear according to claim 7, wherein the first member has less elastic force than the second member.

9. The lower underwear according to claim 1, wherein the crotch portion is joined with the abdomen portion by a front juncture, and wherein the crotch portion is joined with the buttock portion by a rear juncture; and the power tapes extend between the front juncture and the rear juncture.

10. Lower underwear to be put on a body for intimate contact therewith, comprising:
an abdomen portion of the lower underwear partially covering an abdomen of the body;
a crotch portion of the lower underwear including a width partially covering a crotch of the body;
a buttock portion of the lower underwear including an area covering a buttock of the body;
a pair of power tapes provided at least in the crotch portion of the lower underwear, wherein when the lower underwear is placed on a flat surface with a front side disposed upwardly, said power tapes extend on right and left sides of said crotch portion separately with a predetermined spacing therebetween at an inner area of said crotch portion on the front side of the underwear without extending along an edge of said crotch portion; and
wherein the power tapes apply a force to the crotch of the human body such that the abdomen portion, the buttock portion, and the crotch portion having the power tapes embrace the pelvis.

11. The lower underwear according to claim 10, wherein said power tapes extend separately with the predetermined spacing therebetween in such a manner that one of said power tapes extends from a left pubis proximity portion to a left ischium proximity portion of the lower underwear and the other of said power tapes extends from a right pubis proximity portion to a right ischium proximity portion of the lower underwear.

* * * * *